(12) United States Patent
Levine et al.

(10) Patent No.: US 8,383,419 B2
(45) Date of Patent: Feb. 26, 2013

(54) HARVESTING TARGET MATERIALS FROM CENTRIFUGED SUSPENSIONS

(75) Inventors: Robert A. Levine, Guilford, CT (US); Stephen C. Wardlaw, Town of Lyme, CT (US)

(73) Assignees: Robert A. Levine, Guilford, CT (US); Stephen C. Wardlan, Lyme, CT (US)

( * ) Notice: Subject to any disclaimer, the term of this patent is extended or adjusted under 35 U.S.C. 154(b) by 252 days.

(21) Appl. No.: 12/817,012

(22) Filed: Jun. 16, 2010

(65) Prior Publication Data

US 2010/0317106 A1    Dec. 16, 2010

Related U.S. Application Data

(60) Provisional application No. 61/187,508, filed on Jun. 16, 2009.

(51) Int. Cl.
*B01D 21/26* (2006.01)

(52) U.S. Cl. ......... 436/177; 436/174; 210/787; 210/789

(58) Field of Classification Search ................... 210/787, 210/789; 436/177, 174, 172
See application file for complete search history.

(56) References Cited

U.S. PATENT DOCUMENTS

| | | | |
|---|---|---|---|
| 5,460,979 A * | 10/1995 | Levine et al. | ................. 436/523 |
| 5,496,704 A | 3/1996 | Fiedler et al. | |
| 6,197,523 B1 | 3/2001 | Rimm et al. | |
| 6,444,436 B1 | 9/2002 | Rimm et al. | |
| 6,670,197 B2 | 12/2003 | Rimm et al. | |
| 6,911,315 B2 | 6/2005 | Rimm et al. | |
| 7,074,577 B2 | 7/2006 | Haubert et al. | |
| 7,129,056 B2 | 10/2006 | Rimm et al. | |
| 7,220,593 B2 | 5/2007 | Haubert et al. | |
| 7,329,534 B2 | 2/2008 | Haubert et al. | |
| 7,358,095 B2 | 4/2008 | Haubert et al. | |
| 7,397,601 B2 | 7/2008 | Laudo | |
| 7,495,827 B2 | 2/2009 | Grimes et al. | |
| 7,560,277 B2 | 7/2009 | Weller, III | |
| 7,629,176 B2 | 12/2009 | Haubert et al. | |
| 2005/0109716 A1 * | 5/2005 | Leach et al. | .................. 210/787 |
| 2008/0128340 A1 | 6/2008 | Haubert et al. | |
| 2008/0296230 A1 * | 12/2008 | De Wit et al. | ................. 210/687 |
| 2010/0074803 A1 | 3/2010 | Haubert et al. | |

* cited by examiner

*Primary Examiner* — Yelena G Gakh
*Assistant Examiner* — Christopher A Hixson
(74) *Attorney, Agent, or Firm* — Olympic Patent Works PLLC

(57) ABSTRACT

Embodiments of the present invention are directed to harvesting a target material from a suspension using a tube and float system. A suspension suspected of containing a target material is combined with a solution having one or more labels that distinguish the target material from other materials in the suspension. The tube, float, and suspension are centrifuged to separate various materials in the suspension according to associated specific gravities. The float expands the axial length of the target material layer and displaces the target material to a narrow space between the float and the inner wall of the tube. The space is illuminated with light that causes the labels to emit light identifying the location of the target material within the tube. One or more openings can then be formed in the tube at or near the point where the target material is located and the target material harvested.

44 Claims, 13 Drawing Sheets

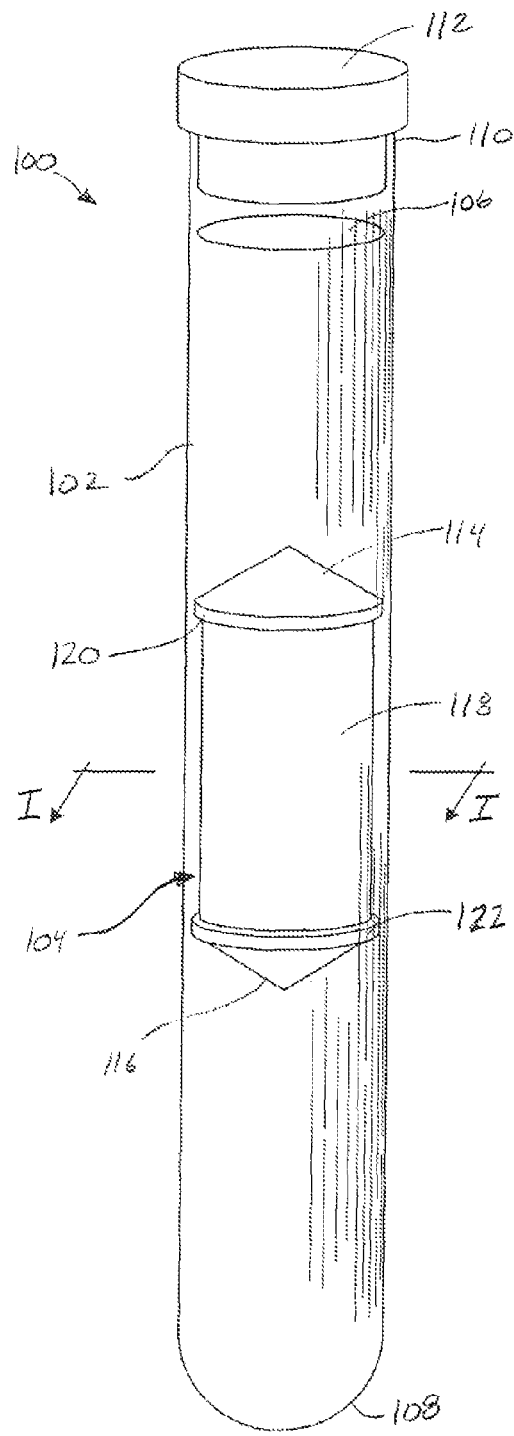
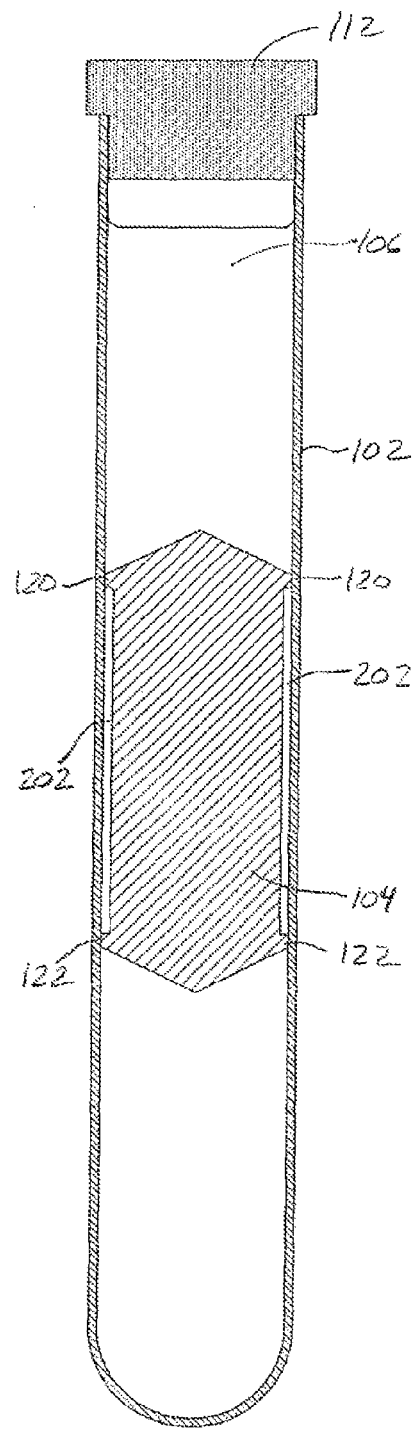
Figure 1
Figure 2

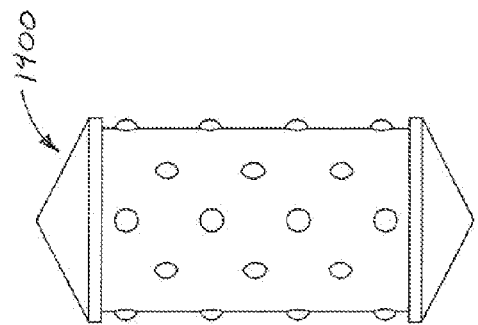
Figure 14
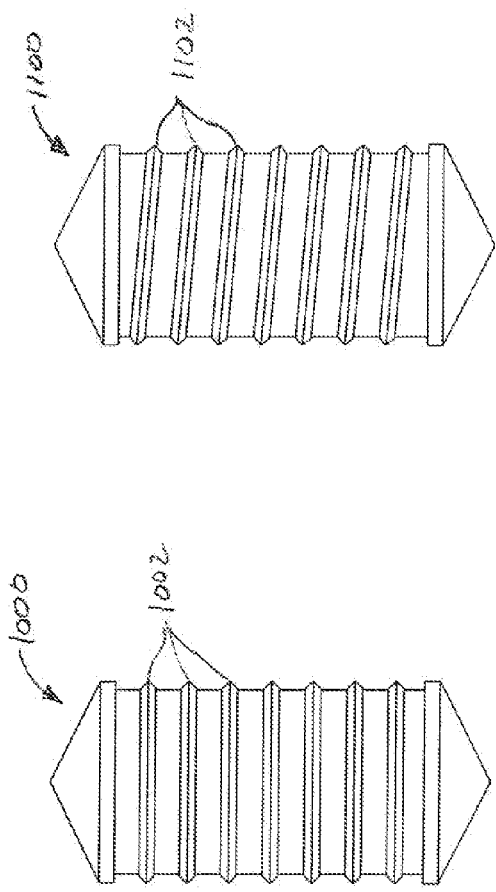
Figure 11
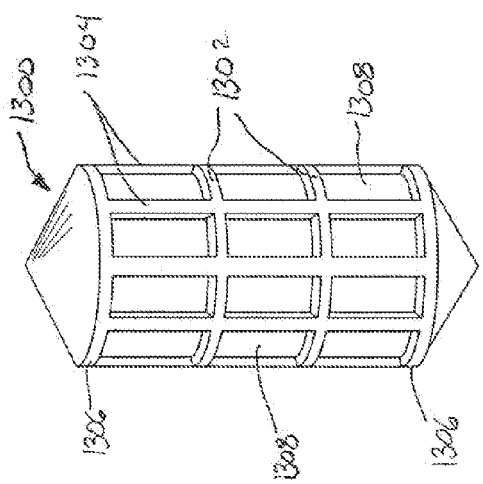
Figure 13
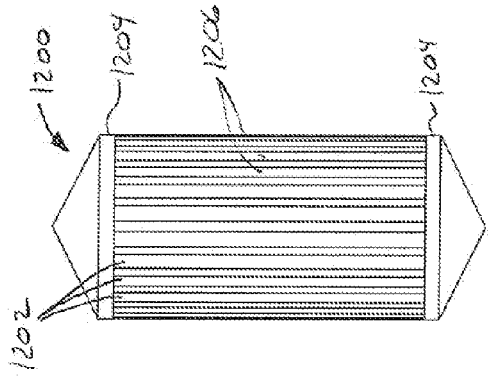
Figure 10
Figure 12

HARVESTING TARGET MATERIALS FROM CENTRIFUGED SUSPENSIONS

CROSS-REFERENCE TO RELATED APPLICATION

This application claims the benefit of Provisional Application No. 61/187,508, filed Jun. 16, 2009.

TECHNICAL FIELD

Embodiments of the present invention relate generally to density-based fluid separation and, in particular, to extraction of target materials found in constituent fluid components of a suspension layered by centrifugation.

BACKGROUND

Blood is a suspension of particulates (e.g., red blood cells and white blood cells) that is routinely examined for the presence of abnormal organisms or cells, such as cancer cells, ova, parasites, microorganisms, and inflammatory cells. Blood is typically analyzed by smearing a sample on a slide and is stained and visually studied usually by bright field microscopy, and then, if needed, by immunologic stains and/or other molecular techniques. Visual detection of cancer cells and other abnormal organisms in smears is often hindered by the presence of extraneous material interspersed between cells. Additionally, standard smear preparations utilize only a fraction of the sample since the smears must be thin enough to allow the passage of light, but the examination of an entire blood sample across multiple smears is often impractical and cost prohibitive in most laboratory settings. Consequently, the sensitivity of disease detection can be limited by the smear methodology.

Blood samples can also be collected to detect a variety of different viruses. For example, HIV, cytomegalovirus, hepatitis C virus, and Epstein-Barr virus can be detected in blood samples using polymerase chain reaction ("PCR")-based or serologic tests. Although PCR-based tests are sensitive and quantitative, PCR-based tests can be cost prohibitive and imprecise because they may detect contaminants or other cross-reacting sequences in the blood sample. Serology on the other hand can also be used to detect the presence of certain viruses, but serology does not provide quantitative information, such as how much of a virus is present?

Practitioners, researchers, those working with suspensions continue to seek systems and methods for accurately analyzing suspensions for the presence or absence of various kinds of particulates.

SUMMARY

Embodiments of the present invention are directed methods of harvesting a target material from a suspension using a tube and float system. A suspension is a fluid containing particulates that are sufficiently large for sedimentation. Examples of suspensions include paint, urine, anticoagulated whole blood, and other bodily fluids. A target material can be cells or particles whose density equilibrates when the suspension is centrifuged. Examples of target materials found in suspensions obtained from living organisms include cancer cells, ova, fetal cells, inflammatory cells, viruses, parasites, and microorganisms, each of which has an associated specific gravity. Initially, a suspension suspected of containing a target material is combined in a tube with a solution, mixture, or other suspension containing one or more labels, such as labeled ligands, configured to distinguish the target material from other materials in the suspension when illuminated with light of appropriate wavelengths. A float is added to the tube, and the tube, float, and suspension are centrifuged together, causing the various materials suspended in the suspension to separate into different layers along the axial length of the tube according to their specific gravities. The float is selected with a specific gravity that positions the float at approximately the same level as the layer containing the target material. If the target material is present, the float is positioned in, and expands the axial length of, the layer in which the target material is present by virtue of their shared density. As a result, nearly the entire quantity of target material is trapped within a narrow space between the float outer surface and the inner surface of the tube. The material trapped within this narrow space is exposed to light that causes the label attached to the target material, if present, to emit light that can be detected and used to distinguish the target material from other materials and identify the location of the target material within the tube. One or more openings can then be formed in the tube at or near the point where the target material is located and the target material harvested.

BRIEF DESCRIPTION OF THE DRAWINGS

FIG. 1 shows an isometric view of a tube and float system in accordance with one embodiment of the present invention.

FIG. 2 shows a cross-sectional view of the tube and float system shown in FIG. 1, along a line I-I, in accordance with one embodiment of the present invention.

FIGS. 6-14 show different types of structures that can be added to the main body of a float in accordance with embodiments of the present invention.

DETAILED DESCRIPTION

Figure 3:
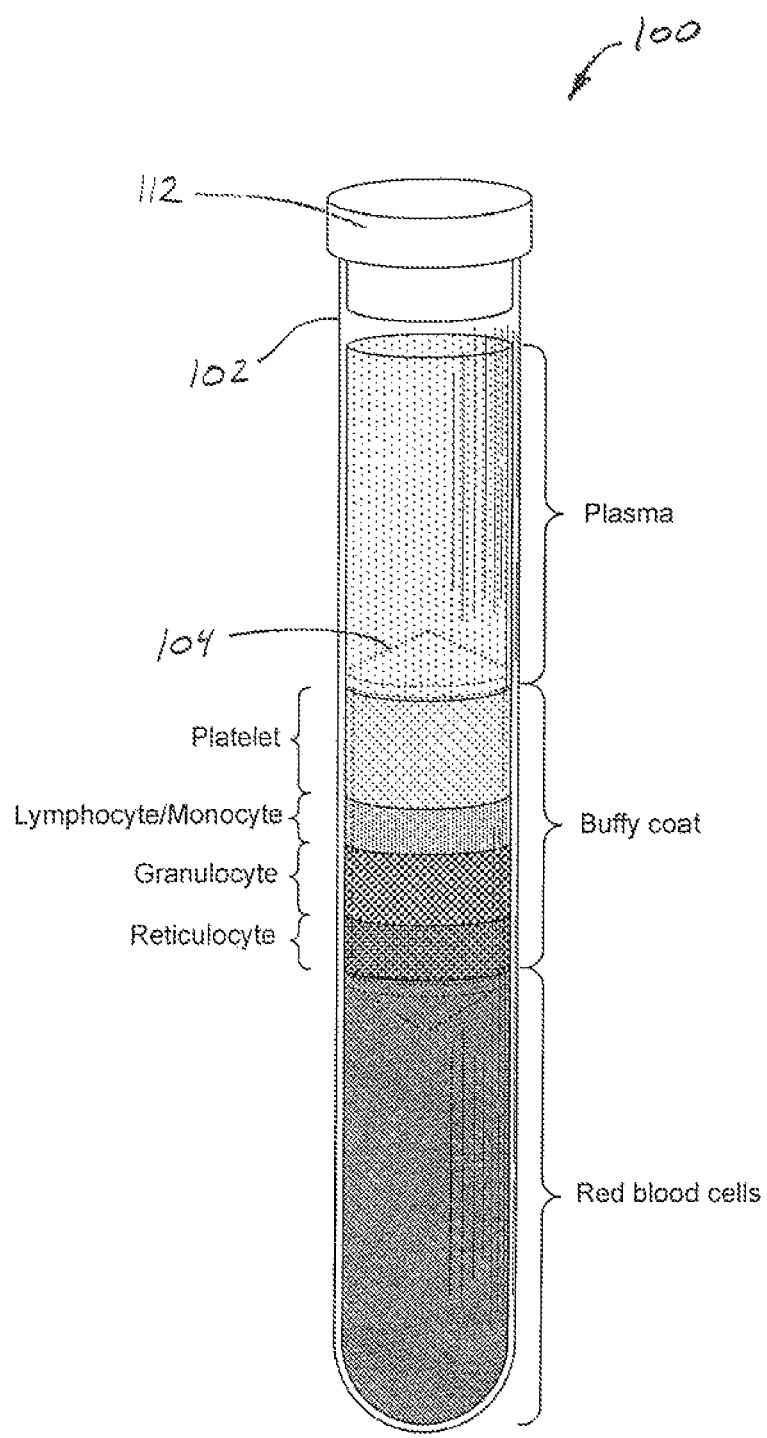
FIG. 3 shows an example of the tube and float system shown in FIG. 1 used to trap and spread a buffy coat of a blood sample in accordance with one embodiment of the present invention.

Embodiments of the present invention are directed methods of harvesting a target material from a suspension centrifuged in a tube and float system. The detailed description of the present invention is organized as follows. A general description of tube and float systems is provided in a first subsection. Methods of labeling target materials in a suspension are described in a second subsection. Methods of accessing and harvesting a target material from a tube and float system are described in a third subsection.

Tube and Float Systems

FIG. 1 shows an isometric view of a tube and float system 100. The system 100 includes a tube 102 and a float 104, which is shown suspended within a fluid 106. The tube 102 has a circular cross-section, a first closed end 108, and a second open end 110. The open end 110 is sized to receive a stopper or cap 112, but the open end 110 can also be configured with threads (not shown) to receive a threaded stopper or screw cap 112 that can be screwed onto the open end 110. The tube 102 can also be configured with two open ends that are both sized and configured to receive stoppers or caps and can be threaded to receive a threaded stopper or screw cap. As shown in FIG. 1, the tube 102 has a generally cylindrical geometry, but may also be configured with a tapered geometry that widens toward the open end 110. The tube 102 can be composed of a transparent or semitransparent material, such as a plastic or glass, and the side wall of the tube 102 is sufficiently flexible or deformable to accommodate expansion in the radial direction due to hydrostatic pressure exerted by the fluid 106 under centrifugal forces. Although the tube 102 has a circular cross-section, in other embodiments, the tube 102 can have an elliptical, a square, a rectangular, an octagonal, or any other suitable cross-sectional shape that substantially extends along the length of the tube 102. The float 104 shown in FIG. 1 includes a first cone-shaped tapered end cap 114, a second cone-shaped tapered end caps 116, a main body 118, and two sealing rings 118 and 120 with approximately equal diameters that are greater than the diameter of the main body 118. The sealing rings 120 and 122 may be separately formed and attached to the main body 118, or the sealing rings 120 and 122 and the main body 118 can form a single structure.

FIG. 2 shows a cross-sectional view of the tube 102 and float 104 along a line I-I, shown in FIG. 1. The sealing rings 120 and 122 are sized to be approximately equal to, or slightly greater than, the inner diameter of the tube 102, and the body 118 is sized to have an outer diameter that is less than the inner diameter of the tube 102, thereby defining an annular gap 202 between the outer surface of the body 118 and the interior sidewall of the tube 102. The body 118 occupies much of the cross-sectional area of the tube 102 with the annular gap 202 sized to substantially contain a target material.

When the tube 102 is centrifuged, the diameter of the tube 102 may expand and the float 104 moves along the central axis of the tube and assumes a position corresponding the float's specific gravity. Once the centrifugation is complete, if the tube 102 has expanded during centrifugation, the tube 102 constricts back down on the sealing rings 120 and 122. The size of the annular gap 202 is determined by the distance between of the sealing rings 120 and 122 and the distance between the outer surface of the body 118 and the inner wall of the tube 102. The sealing rings 120 and 122 substantially seal a portion of the target material within the annular gap 202. The seal formed between the sealing rings 120 and 122 and the inner wall of the tube 102 may form a fluid-tight seal. The term "seal" encompasses near-zero clearance or slight interference between the sealing rings 120 and 122 and the inner wall of the tube 102. The sealing rings 120 and 122 also provide a support structure for the tube 102. As shown in the embodiments of FIGS. 1 and 2, the sealing rings 120 and 122 can be continuous ridges, enabling the fluid 106 to be centrifuged at lower speeds and slumping of the separated layers is inhibited. Note that in alternative embodiments the sealing rings 120 and 122 can be omitted or the ridges of the sealing rings 120 and 122 that make contact with the inner wall of the tube 102 can be discontinuous or segmented bands with one or openings providing the fluid 106 at least one path in and out of the annular gap 202.

FIG. 3 shows an example of the tube and float system 100 used to trap and spread a buffy coat of an anticoagulated whole blood sample. When a blood sample is centrifuged without a float, the blood separates into a thin buffy coat layer located between a blood cell layer and a plasma layer. In particular, the blood sample after centrifugation is separated into six layers: (1) packed red cells, (2) reticulocytes, (3) granulocytes, (4) lymphocytes/monocytes, (5) platelets, and (6) plasma. The reticulocyte, granulocyte, lymphocytes/monocyte, platelet layers form the buffy coat and are the layers often analyzed to detect certain abnormalities and cancer. However, the layers comprising the bully coat are thin and can be difficult to extract for analysis. On the other hand, in using the system 100, prior to centrifuging the blood sample, the float 104 is selected with a specific gravity that positions the float at approximately the same level as the buffy coat. The float 104 is then inserted into the tube 102 followed by introducing the blood sample to the tube 102, or the float 104 can be inserted after the blood sample has been introduced to the tube 102. The tube 102, blood sample, and float 104 are then centrifuged for an appropriate period of time (e.g., approximately 5 minutes), enabling the materials of the blood sample to separate axially into layers along the length of the tube 102 according to the specific gravity associated with each material. As shown in the Example of FIG. 3, centrifugation is stopped, the float 104 expands the buffy coat between the main body 118 of the float and the inner wall of the tube 102, enabling the expanded buffy coat to be analyzed through the tube 102.

The float 104 can be composed of the same materials or composed of different materials. The material used to form the float 104 include, but are not limited to, rigid organic or inorganic materials, and rigid plastic materials, such as polystyrene, acrylonitrile butadiene styrene ("ABS") copolymers, aromatic polycarbonates, aromatic polyesters, carboxymethylcellulose, ethyl cellulose, ethylene vinyl acetate copolymers, nylon, polyacetals, polyacetates, polyacrylonitrile and other nitrile resins, polyacrylonitrile-vinyl chloride copolymer, polyamides, aromatic polyamides ("aramids"), polyamide-imide, polyarylates, polyarylene oxides, polyarylene sulfides, polyarylsulfones, polybenzimidazole, polybutylene terephthalate, polycarbonates, polyester, polyester imides, polyether sulfones, polyetherimides, polyetherketones, polyetheretherketones, polyethylene terephthalate, polyimides, polymethacrylate, polyolefins (e.g., polyethylene, polypropylene), polyallomers, polyoxadiazole, polyparaxylene, polyphenylene oxides (PPO), modified PPOs, polystyrene, polysulfone, fluorine containing polymer such as polytetrafluoroethylene, polyurethane, polyvinyl acetate, polyvinyl alcohol, polyvinyl halides such as polyvinyl chloride, polyvinyl chloride-vinyl acetate copolymer, polyvinyl pyrrolidone, polyvinylidene chloride, specialty polymers, and so forth, and most preferably polystyrene, polycarbonate, polypropylene, acrylonitrite butadiene-styrene copolymer ("ABS") and others.

Figure 4A:
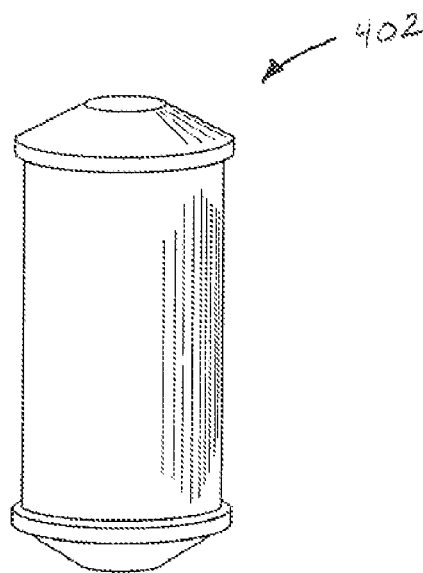
FIGS. 4A-4C each show one of three different geometric shapes for float end caps in accordance with embodiments of the present invention.
Figure 4B:
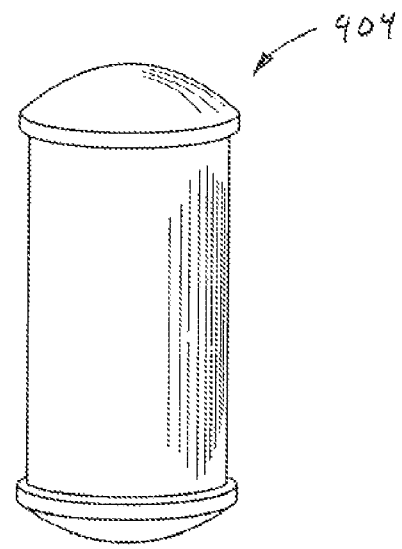
Figure 4C:
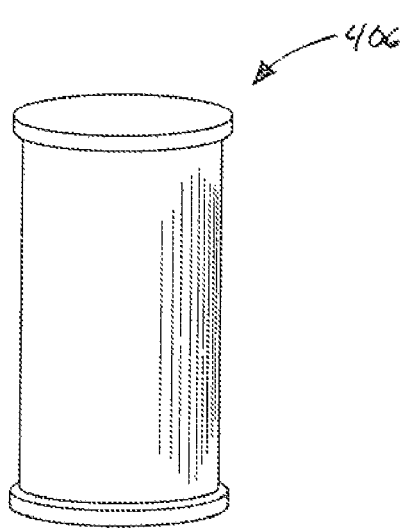

As shown in FIGS. 1-3, the float 104 is configured with cone-shaped end caps that direct the flow of the fluid contained in the tube around the float during centrifugation. However, embodiments of the present invention include other types of end cap shapes. FIGS. 4A-4C each show one of three different geometric shapes for float end caps. In FIG. 4A, a float 402 includes truncated cone-shaped end caps. In FIG. 4B, a float 404 includes convex or dome-shaped end caps. In FIG. 4C, a float 406 includes flat or planar end caps. Embodiments of the present invention include many other geometrical shapes for the end caps including concave or convex configurations and providing a curved, sloping, and/or tapered surface around which the fluid may flow during centrifugation. Alternative embodiments include, but are not limited to, tectiform and truncated tectiform; three, four, or more sided pyramidal and truncated pyramidal; ogival or truncated ogival; and geodesic shapes.

Figure 5:
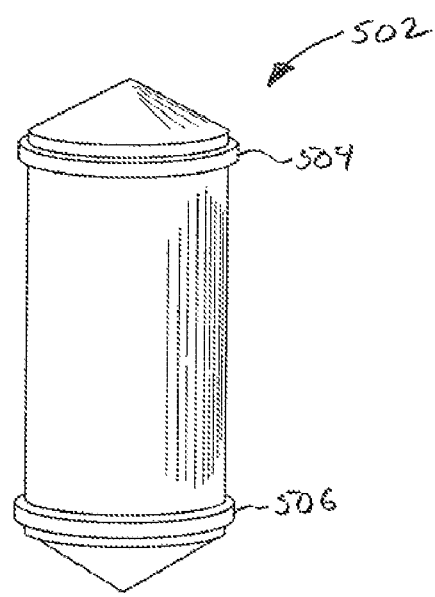
FIG. 5 shows an example of a float with two sealing rings axially displaced from the end caps in accordance with one embodiment of the present invention.

Floats are also not limited to the sealing rings being located at the ends of the float as shown in 1-4. In alternative embodiments, the sealing rings can be located anywhere along the length of the float main body. FIG. 5 shows an example of a float 502 with the sealing rings 504 and 506 axially displaced from the end caps.

In alternative embodiments, the main body of a float can be configured with a variety of different support structures and structures for separating target materials or directed the fluid around the float during centrifugation. FIGS. 6-14 show just nine examples of different types of structures that can be added to the body of the float exterior.

Figure 6:
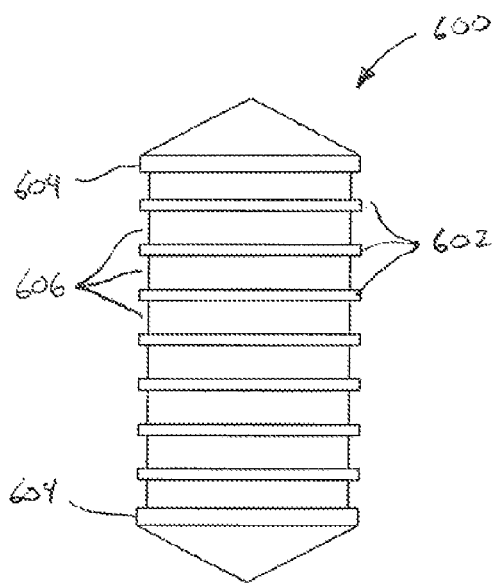

In FIG. 6, the body of a float 600 includes a number of regularly spaced continuous annular ribs 602. The ribs and sealing ridges 604 are configured to provide a sealing engagement with the inner wall of the tube when centrifugation is stopped. The ribs also form annular-shaped channels 606 between the ribs. Although, the ribs 604 shown in FIG. 6 are continuous ribs, in other embodiments, the ribs can be broken or segmented to allow fluid to flow between annular channels 606. In various embodiments, the number of ribs, rib spacing, and rib thickness can each be independently varied.

Figure 7:
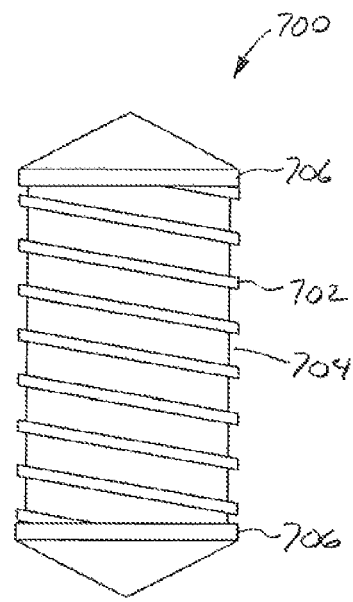

In FIG. 7, the body of a float 700 includes a continuous helical structure or ridge 702 creating a helical channel 704 that wrap the length of the main body between sealing ridges 706. In other embodiments, the helical ridge 702 can be broken or segmented to allow fluid to flow between adjacent turns in the helical channel 704. In various embodiments, the helical rib spacing and rib thickness can all be independently varied.

Figure 8:
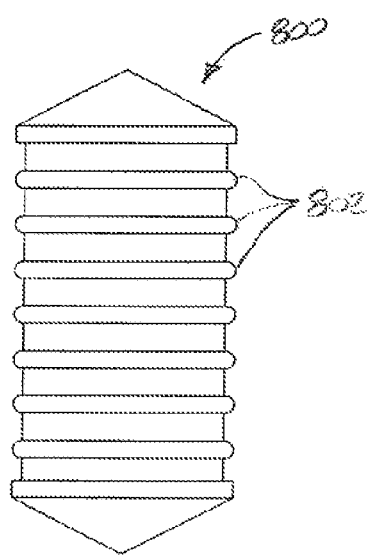
Figure 9:
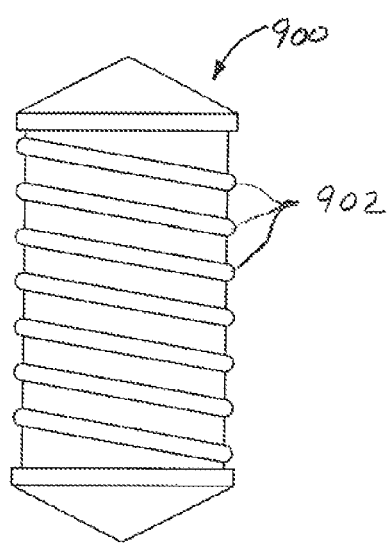

The floats 800 and 900, shown in FIGS. 8 and 9 respectively, are similar to the float exteriors 600 and 700, shown in FIGS. 6 and 7, but the annular ribs 802 of the float exterior 800 and helical rib 902 of the float exterior 900 are curved or have a rounded profile.

The floats 1000 and 1100, shown in FIGS. 10 and 11 respectively, are also similar to the float exteriors 600 and 700, shown in FIGS. 6 and 7, but the annular ribs 1002 of the float exterior 1000 and helical rib 1102 of the float exterior 1100 are radially tapered.

In FIG. 12, the body of a float 1200 includes a number of radially spaced, axially oriented splines 1202. The splines and scaling ridges 1204 are configured to provide a sealing engagement with the inner wall of the tube when centrifugation is stopped. The open regions between splines 1202 are fluid retention channels 1206 that trap fluid between the inner wall of the tube and the body of the float exterior 1200. The surfaces of the body between the splines can be flat, curved, or have other geometric shapes. In alternative embodiments, the number of splines, spline spacing, and spline thickness can each be independently varied. The splines 1202 and/or sealing rings 1204 can also be broken or segmented.

In FIG. 13, the body of the float 1300 includes a network of intersecting annular ribs 1302 and splines 1304. The sealing rings 1306 and network of annular ribs 1302 and splines 1304 extend from the main body to form a support structure for the deformable tube, and the ribs and splines also form a number of fluid retention chambers 1308 formed between the inner wall of the tube and the body of the float exterior. The surfaces of the body associated with the retention chambers can be flat or curved. In alternative embodiments, the number of ribs and splines, rib and spline spacing, and rib and spline thickness can each be independently varied. The ribs 1302 and splines 1304 can also be broken or segmented to allow fluid to flow between chambers. The sealing rings 1306 can also be broken or segmented. The spacing of the splines and ribs can vary to suit various applications. For example the spacing can range from approximately 100 µm to approximately 5,000 µm. Furthermore, if the annular free space is 50 µm and there are ribs and splines each spaced approximately 3,000 µm, the volume of a chamber is approximately 0.5 µL. A 0.5 µL chamber containing a blood sample represents a concentration of approximately 20,000 times by volume for a blood sample volume of 10 mL. A chamber of this size contains hundreds of thousands of cells, where the original 10 mL blood sample may contain a total of 70,000 or more white blood cells and 50 billion red blood cells.

In FIG. 14, the body of the float exterior 1400 includes a number of protrusions 1402 that provide support for the deformable tube. In alternative embodiments, the number and pattern of protrusions can be varied.

Tube and float systems described are intended to provide only a representation of the kinds of system methods of the present invention can be applied. Further variations on the tube and float systems are described in U.S. Pat. No. 7,074,577 issued Jul. 11, 2006, and U.S. Pat. No. 7,329,534 issued Feb. 12, 2008.

In alternative embodiments, the float includes a pressure release system to alleviate pressure that builds up in the fluid trapped below the float during centrifugation. The release system prevents the material or particles trapped in the fluid below the float from being forced into the annular gap, which contains the target material.

Figure 15A:
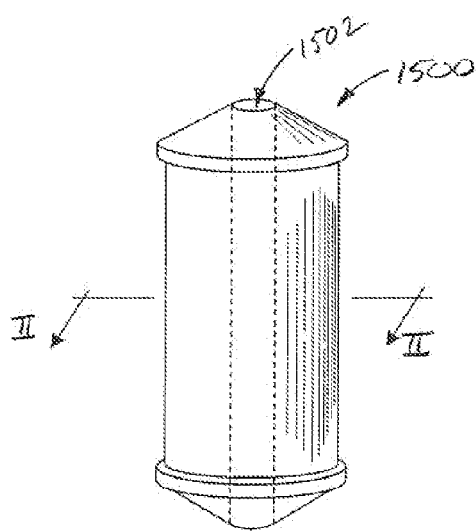
FIG. 15A shows an isometric view of a float with a central axis bore in accordance with one embodiment of the present invention.
Figure 15B:
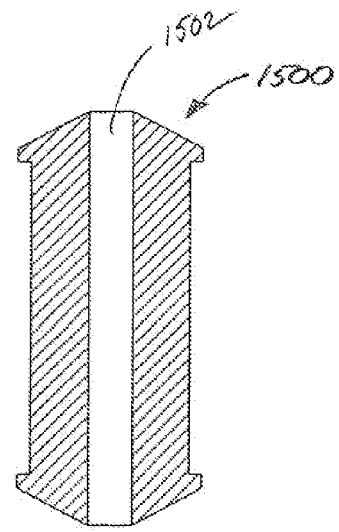
FIG. 15B shows a cross-sectional view of the float shown in FIG. 15A, along a line II-II, in accordance with one embodiment of the present invention.

FIG. 15A shows an isometric view of float 1500, and FIG. 15B shows a cross-sectional view of float 1500 along a line II-II, shown in FIG. 15A. The float 1500 is nearly identical to the float 104, except the float 1500 includes bore 1502 that extends axially through the float 1500. When the tube/float system is centrifuged, the tube expands, freeing the float 1500 in the fluid. As centrifugation is slowed, pressure may build up in the fluid fraction trapped below the float 1500. This pressure may cause fluid to be forced into the annular gap 202 described above containing the captured target material, thus making detection of the contents of the target material more difficult. Alternatively, the collapse of the side wall of the sample tube during deceleration may produce excessive or disruptive fluid flow through the annular gap 202. The bore 1502 allows for any excessive fluid flow or any resultant pressure in the dense fractions trapped below the float 1500 to be relieved. The excessive fluid flows into the bore 1502, thus preventing degradation of the trapped target material.

Figure 16A:
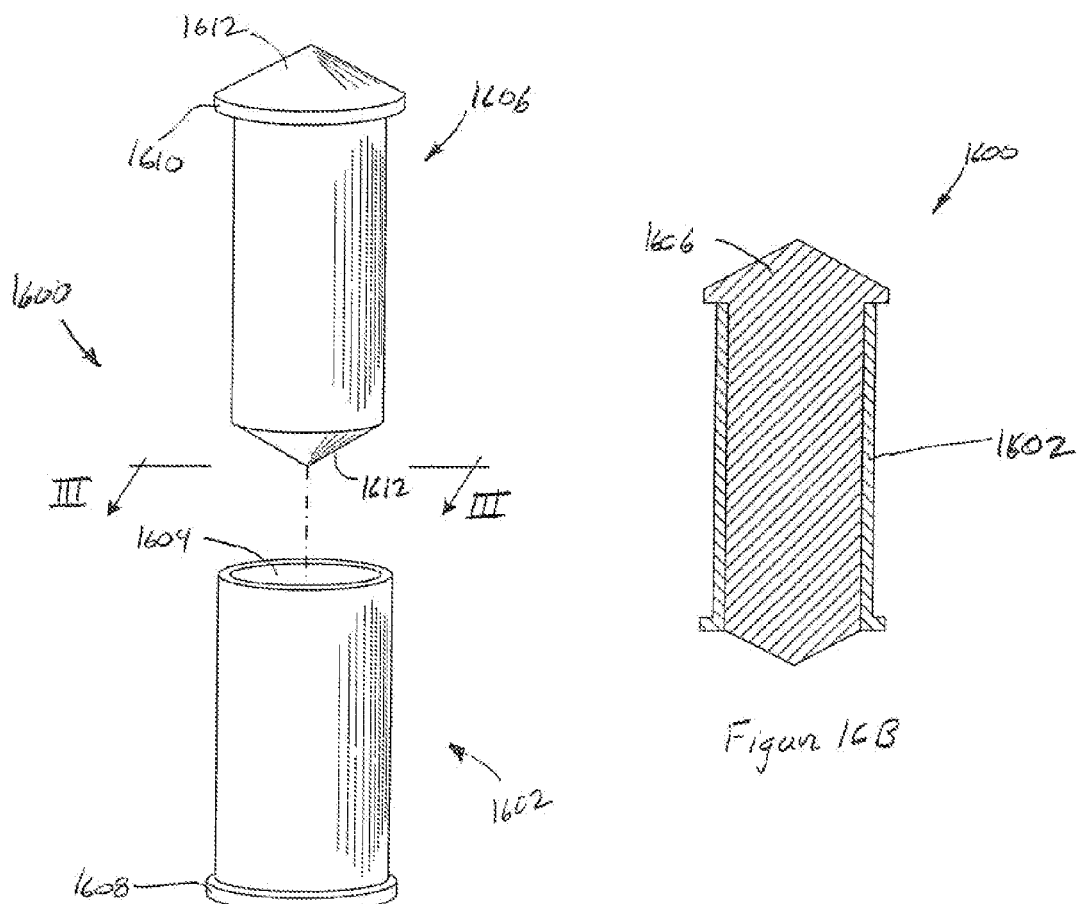
FIG. 16A shows an isometric view of a two-piece float in accordance with one embodiment of the present invention.

FIG. 16A shows an isometric view of a two-piece float 1600. The float 1600 includes a main body portion or sleeve 1602 with a central bore 1604, which is sized to slidably receive a second, piston-like center portion 1606. The sleeve 1602 includes a sealing ring 1608, which is located along the lower or bottom end of the sleeve 1602. A sealing ridge 1610 is disposed at the upper end of the piston section 1606. Optionally cone-shaped tapered ends 1612 are located at the upper and lower ends of the piston 1606 to facilitate and direct the flow of fluid and material past the sealing ridges 1608 and 1610 during centrifugation.

Figure 16B:
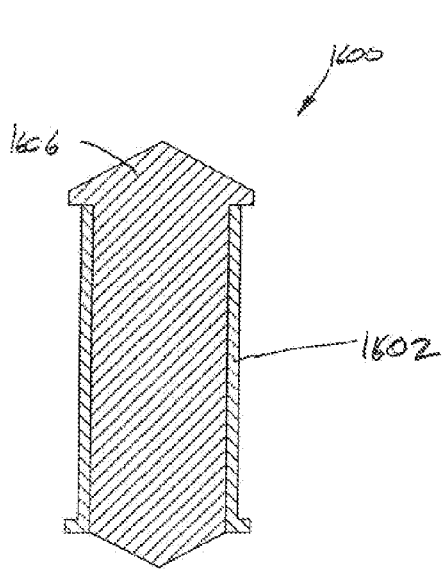
FIG. 16B shows a cross-sectional view of the float shown in FIG. 16, along a line in accordance with one embodiment of the present invention.

FIG. 16B shows a cross-sectional view of the float 1600 along a line III-III, shown in FIG. 16A, with the piston 1606 inserted into the bore 1604. The piston 1606 is fully received within the bore 1604. The float 1600 is oriented in the tube so that the sealing ridge 1610 is at the top and the sealing ridge 1608 is toward the bottom of the tube. The two portions may be formed of the same material or different materials, so long as the overall specific gravity of the float 1600 enables the float to be positioned at the same level as a layer containing the target material. The piston 1606 can be formed of a slightly higher specific gravity material than the sleeve 1602, which insures that the two portions stay together during centrifugation. Alternatively, the two float members are formed of the same material and/or a frictional fit sufficient to keep the float members together during centrifugation.

As the tube containing the fluid and float 1600 is centrifuged, the two pieces 1602 and 1606 stay together and act in the same manner as a one-piece float to axially expand the target material. When separation and layering of the fluid components is complete and centrifugation is slowed, pressure may build in the fluid trapped below the float 1600, e.g., where contraction of the tube continues after initial capture of the float by the tube wall. Any such pressure in the trapped fluid forces the piston 1606 upward, thus relieving the pressure, and thereby preventing the fluid from breeching the seal between the sealing ring 1608 and the tube wall.

Other examples of floats configured to relieve the pressure created by fluid trapped below the float are described in U.S. Pat. No. 7,220,593 issued May 22, 2007 and U.S. Pat. No. 7,358,095 issued Apr. 15, 2008.

Labeling and Identifying Target Materials

Methods of the present invention provide a means of harvesting an identified target material or particles of a target material present in a centrifuged suspension. A suspension is a fluid containing particulates that are sufficiently large for sedimentation. Examples of suspensions include paint, urine, anticoagulated whole blood, and other bodily fluids. A target material can be cells or particles whose density equilibrates when the suspension is centrifuged. Examples of target materials found in suspensions obtained from living organisms include cancer cells, ova, fetal cells, inflammatory cells, viruses, parasites, and microorganisms, each of which has an associated specific gravity. A target material can be identified in a suspension by attaching a suitable label to the target material prior to centrifuging the suspension. The labels distinguish the target material from other materials present in the suspension. Examples of suitable labels include quantum dots, fluorophores, or other detectable labels including, but not limited to, Rhodamine, Fluorescein, Cy3, Cy5, sulforhodamine 101 acid chloride ("Texas Red"), Bodipy. The labels can be coupled to antibodies, antigens or other suitable molecules for attaching a target material, either directly, or after being encapsulated in liposomes or other biological substrates. Consider for example the use of labels to identify tumor cells in blood. Evidence indicates that tumor cells are shed from a tumor mass at the earliest stages of malignant progression*. Some of these cells, also called "rare cells," travel via the blood to sites anatomically distant from the tumor and may form metastases. Because rare cells are present in such low numbers, rare cells can escape detection using standard methods of investigation such as microscopic examination of routinely stained cyto/histology slides. However, rare cells can be identified by attaching a suitable light emitting label to epitopes on the rare cell surface or by attaching a label to intracellular epitopes or by attaching a label to specific nucleotide sequences. Examples of attaching labels to epitopes are described in "Biodegradable Quantum Dot Nano Composites Enable Live Cell Labeling and Imaging of Cytoplasmic Targets," Betty Y. S. Kim et al., Institute of Biomaterials and Biomedical Engineering, University of Toronto, 164 College Street, Toronto, Ontario M5S 3G9, Canada, Terence Donnelly Centre for Cellular Biomolecular Research, University of Toronto, 160 College Street, Toronto, Ontario M5S 3E1, Canada, and Division of Neurosurgery, the Hospital for Sick Children, University of Toronto, 555 University Ave., Toronto, Ontario M5G 1X8, Canada. Nano Lett., 2008, 8(11), pp 3887-3892. DOI: 10.1021/NL802311t. Publication date (Web): Sep. 25, 2008. Copyright 2008 American Chemical Society.

When a label is exposed to light of a certain wavelength or frequency, the label emits light (e.g., in the visible spectrum or optically detectable spectrum) with a different wavelength or frequency that can be readily detected and used to indicate the presence of the target material. A label is attached to a molecule with a configuration that specifically binds to the target material. A solution, mixture, or other suspension containing one or more labels, such as labeled ligands, is added to the suspension, the labels are allowed adequate time to bind to a target material present in the suspension, and the tube, float and suspension are centrifuged. After the suspension containing a labeled target material is centrifuged, the labeled target material is localized in the annular gap between the main body of the float and the inner wall of the tube. The target material can be constrained from migration by the viscosity of other compacted materials. In alternative embodiments, the target material can be further constrained to channels or chambers formed by structures such as the ribs and/or splines described above with reference to FIGS. 6-14. The location of the labeled target material, as well as the radial coordinates of the labeled target material, can be determined, numbered, stored electronically, and recorded by an instrument configured to detect and/or capture images of the labeled target material. In other embodiments, the location on the tube from which light is emitted by a label can be marked to identify the location of the target material trapped between the float and the inner wall of the tube.

Figure 17:
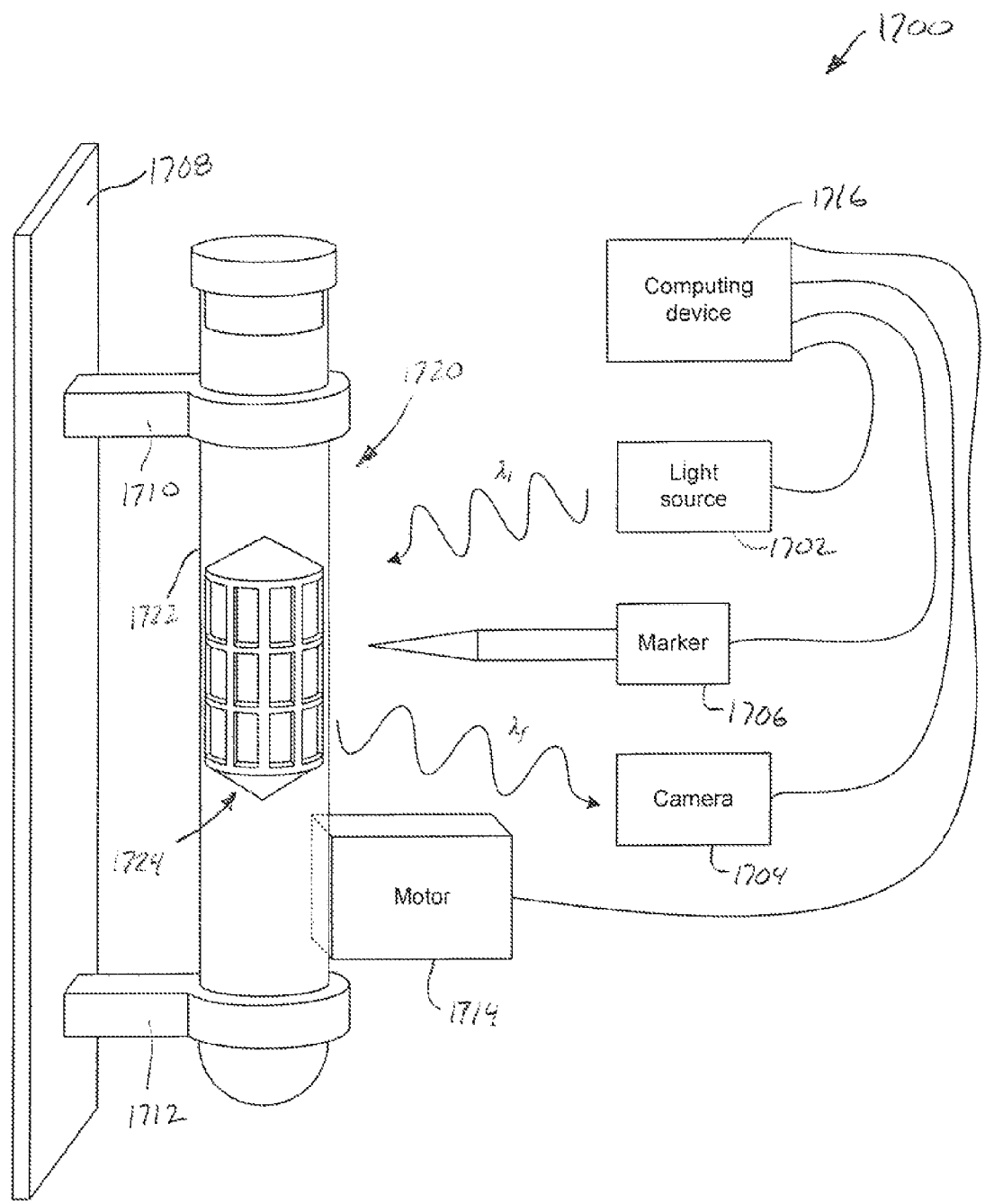
FIG. 17 shows an automated detection system for identifying a labeled target material in a tube and float system in accordance with one embodiment of the present invention.

FIG. 17 shows an automated detection system 1700 for identifying the location of a labeled target material in a tube and float system. The detection system 1700 includes a light source 1702, a camera 1704, an optional marker 1706, a stage 1708, two supports 1710 and 1712, and a motor 1714. The system 1700 also includes a computing device 1716 connected to, and configured to control the operation of, the light source 1702, the camera 1704, the marker 1706 and the motor 1714. A tube and float system 1720 is disposed within the supports 1710 and 1712. In the example of FIG. 17, the float 1724 includes a rib and spline structure that forms chambers, as described above with reference to FIG. 13. In operation, the tube 1722 can include a centrifuged suspension with one or more labeled target materials trapped within one or more chambers of the float 1724. The light source 1702 illuminates the main body of the float 1724 while the motor 1714 rotates the tube 1722 in either a forward or reverse direction. The camera 1704 captures images of the wavelengths of light emitted from the system 1720 as the tube 1722 is rotated. The camera 1704 can store the images or the images can be sent to the computing device 1716 where the images are stored. The light source 1702 can be operated to selectively direct different excitation light beams at the tube 1722, each beam having a different wavelength. Thus, the light source 1702 and camera 1704 allow one to selectively control and vary the wavelength of the light emitted from the light source 1702 and the wavelengths of light captured by the camera 1704. For example, the light source 1702 can be operated to emit light with a wavelength $\lambda_f$ that stimulates emission of light with a wavelength $\lambda_f$ from a label attached to a target material, which is in turn captured and recorded by the camera 1704. It may also be the case that one or more wavelengths are emitted from the labels attached to the target material and other wavelengths are emitted from other labels attached to different materials present in the suspension. Thus, the various wavelengths are captured, by the camera 1704, stored, and sorted in order to indentify the one or more wavelengths of light emitted from the labels attached to the target material particles. As the tube and float system 1722 is rotated, places or coordinates along the tube 1722 from which light $\lambda_f$ is emitted are identified. For example, the computing device 1716 can engage the optional marker 1706 to mark the outer surface of the tube 1722 at approximately the place from which the light $\lambda_f$ is emitted. In other embodiments, the marker 1706 can be omitted and both radial and axial coordinates are recorded or stored in memory with respect to an indexing mark defining the origin of a radial coordinate system. For example, the coordinates used to identify the location of light emitted from a labeled target material particle can be cylindrical coordinates. Each set of recorded radial and axial coordinates corresponds to a place on the surface of the tube from which the labels attached to the target material particles emit light and identifies a location of one or more target material particles.

Examples of other kinds of systems and methods for illuminating and identifying a target material in a tube and float system are described in U.S. Pat. No. 6,197,523 issued Mar. 6, 2001; U.S. Pat. No. 6,670,197 issued Dec. 30, 2003; U.S. Pat. No. 6,911,315 issued Jun. 28, 2005; U.S. Pat. No. 7,129,056 issued Oct. 31, 2006; U.S. Pat. No. 7,397,601 issued Jul. 8, 2008; and U.S. Pat. No. 6,444,436 issued Sep. 3, 2002; and U.S. Pat. No. 7,560,277 issued Jul. 14, 2009.

Embodiments of the present invention are not limited to an automated process of determining the presence of a target material and/or marking the place on the tube 1722 where the target material is located. In alternative embodiments, the marker 1706, camera 1704, and motor 1714 can be omitted and an operator can rotate the system 1720 by hand while the tube is illuminated by the light source 1702. If the light $\lambda_f$ emitted through the tube wall is in the visible portion of the electromagnetic spectrum, the operator can mark the corresponding outer surface of the tube 1722 using a pen or marker to identify the location of the target material.

An example of using the detection system 1700 to locate rare cells in a blood sample contained in the tube 1722 is now described. The system 1700 can also be operated to confirm the malignant or benign nature of observed suspicious cells in situ in the blood sample. A venous or capillary sample of anticoagulated whole blood is drawn into the tube 1722 and float 1724 assembly. The blood sample is combined with a fluorescent morphological stain, such as acridine orange, either before or after being drawn into the tube 1722, so that morphological characteristics of nucleated cells which are observed in the blood sample can be analyzed. The blood sample can also be combined with an epithelial cell-specific label which is used to determine whether any suspicious cells noted in the blood sample are of epithelial origin. This confirmation procedure is chosen because the tumorous cancer cells being assayed are typically epithelial cells. An antigen that is highly specific to a surface receptor on epithelial cells in E-cadherin. In order to label any epithelial cells Cy3 can be used and conjugated directly to E-cadherin. The Cy3 is a label that fluoresces at a different wavelength than acridine orange. The admixture of anticoagulated whole blood, acridine orange, and E-cadherin/Cy3 is centrifuged for a time period of approximately five minutes in the tube and float system 1720. The centrifuged sample is then placed in the supports 1710 and 1712 on the stage 1708. The light source 1702 illuminates the tube 1722 and float 1724 as the tube 1722 is rotated and reciprocated back and forth. Separate scans can be performed in order to distinguish labeled cells. A first scan differentially fluoresces the acridine orange stain added to the sample. This scan produces images of all nucleated cells in the zone of the blood sample being scanned. A second scan is used to differentially fluoresce the E-cadherin/Cy3 label. This scan produces images of the nucleated cells in the scanned zone of the blood sample which are epithelial cells.

Note that rare cells are so rare they may not actually form a layer in a centrifuged blood sample. Rare cells by virtue of slight variations in their density may be located in a layer of surrounding fluid, cells and or particles. Generally rare cells are located in the immediate vicinity of the buffy coat or slightly above it at the plasma platelet interface or slightly below it at the red cell granulocyte interface. Rare cells may, if they are intraerythrocyte parasites, be below the granulocyte red cell interface.

The light source 1702 and camera 1704 can include filter combinations that can be used for additional scans depending on what additional cellular information is being sought. Such additional useful information could include additional cancer cell-specific epitopes enabling a cytopathologist to identify the origin of the cancer cells, i.e., whether they are prostate cancer cells, breast cancer cells, lung cancer cells, ovarian cancer cells, or the like, which epitopic information is presently available, or becomes known in the future. The analysis of the blood sample can be made automatically by the instrument shown in FIG. 17, or it can be performed by visually scanning the sample. The scanning steps and the analysis of the results of the scanning steps can be performed in either order. Scanning of the acridine orange-highlighted cells allows one to identify all of the nucleated cells in the scanned zone, and also allows one to analyze the morphology of the nucleated cells in order to identify any cells which appear to have a morphology which suggests malignancy. Scanning of the E-cadherin/Cy3 highlighted cells allows one to identify which of the nucleated cells in the scanned zone are epithelial cells. Confirmation of the presence of an epithelial cell (E-cadherin/Cy3-highlighted) having abnormal cell morphology (acridine orange-highlighted) in the centrifuged blood sample alerts the cytopathologist to the strong likelihood of a cancerous tumor in the blood sample donor. A similar protocol can be employed to determine whether suspicious nucleated cells are hematologic progenitor cells. The cancerous tumor cells can then be precisely harvested from the tube and float system 1720 without damaging the cell biochemistry for further analysis as described below in the next subsection.

Harvesting Target Materials

Figure 18B:
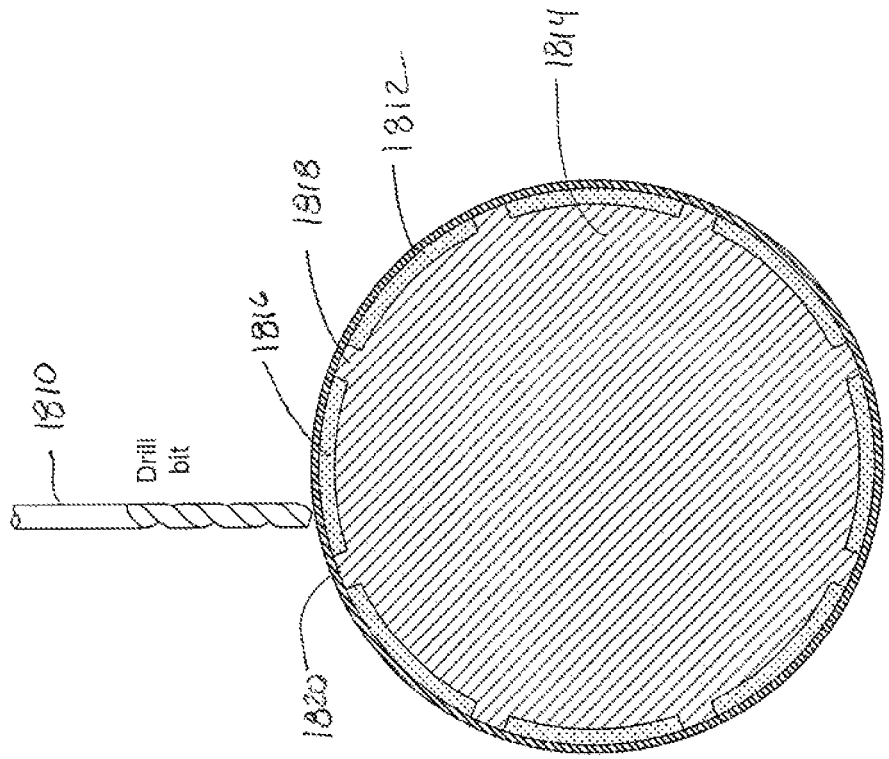
FIG. 18B shows an enlarged cross-sectional view of a tube and a float with a drill bit positioned to form an opening in the tube wall in accordance with one embodiment of the present invention.
Figure 18A:
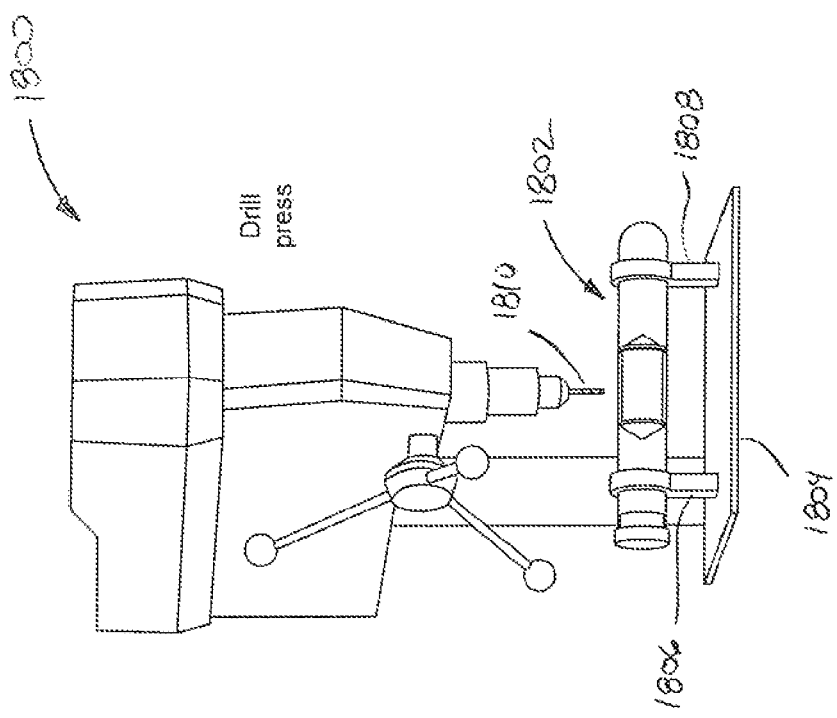
FIG. 18A shows an example of a drill press used to form an opening in a tube wall of a tube and float system in accordance with one embodiment of the present invention.

After one or more locations along the tube of a tube and float system have been marked or the coordinates identified as containing a target material, the target material can be harvested by creating one or more openings in the tube wall, with each opening formed in close proximity to the location of the target material. In certain embodiments, openings can be formed by drilling access holes in the tube wall in close proximity to the target material location. FIG. 18A shows an example of a drill press 1800 used to form an opening in a tube wall of a tube and float system 1802. As shown in FIG. 18A, the system 1802 is mounted on a stage 1804 with supports 1806 and 1808 that hold the system 1802 in place beneath the drill bit 1810 while the drill press 1800 is operated to form an access hole in the tube wall at a desired location. FIG. 18B shows an enlarged cross-sectional view of a tube 1812 and a float 1814 of the system 1802, shown in FIG. 18A, with a drill bit 1810 positioned to form an opening in the tube 1812 wall. The opening gives access to the fluid 1816 filling a chamber formed by splines 1816 and 1818, two ribs (not shown), the tube 1812 wall, and main body of the float 1814. In alternative embodiments, openings can also be formed in a tube wall using a hand-held drill rather than using the drill press 1800.

Figure 19B:
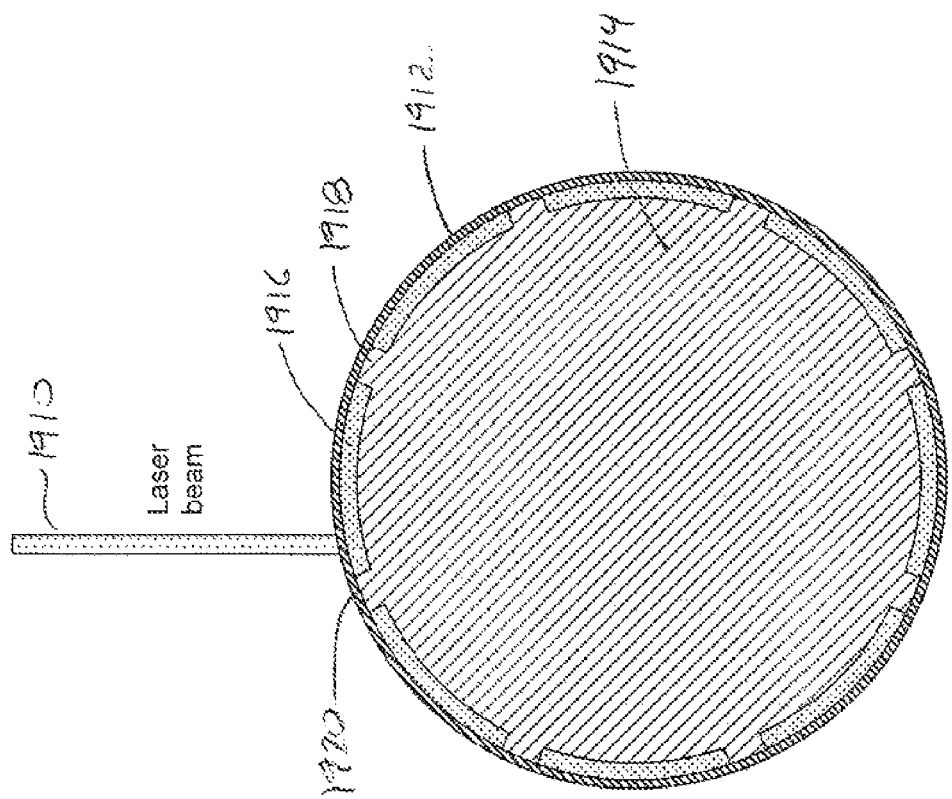
FIG. 19B shows an enlarged cross-sectional view of a tube and a float with a laser beam machining a spot on the tube wall in accordance with one embodiment of the present invention.
Figure 19A:
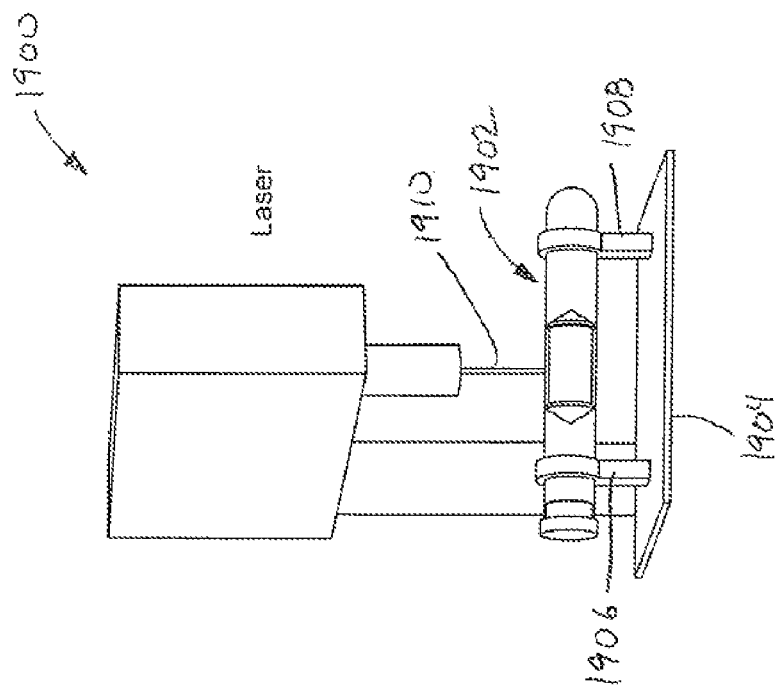
FIG. 19A shows an example of a laser that produces a laser beam that forms an opening in a tube wall of a tube and float system in accordance with one embodiment of the present invention.

In alternative embodiments, the openings can be formed by laser machining the tube wall. FIG. 19A shows an example of a laser 1900 that produces a laser beam with a frequency that can be used to form an opening in a tube wall of a tube and float system 1902. As shown in FIG. 19A, the system 1902, like the system 1802, is mounted on a stage 1904 with supports 1906 and 1908 that hold the system 1902 in place beneath a laser beam 1910 produced by the laser 1900. FIG. 19B shows an enlarged cross-sectional view of a tube 1912 and a float 1914 of the system 1902 with a laser beam machining a spot on the tube wall. Laser machining forms an opening in the tube 1912 wall giving access to a fluid 1916 filling a chamber formed by splines 1918 and 1920, two ribs (not shown), the tube 1912 wall, and main body of the float 1914.

In still other embodiments, an opening can be formed in a tube wall by puncturing the wall with a pointed objected, such as needle or other sharp instrument. An opening can also be formed in the tube wall by melting the wall at a specific location using a heating element, such as heated needle or another type of heated sharp instrument.

Figure 20A:
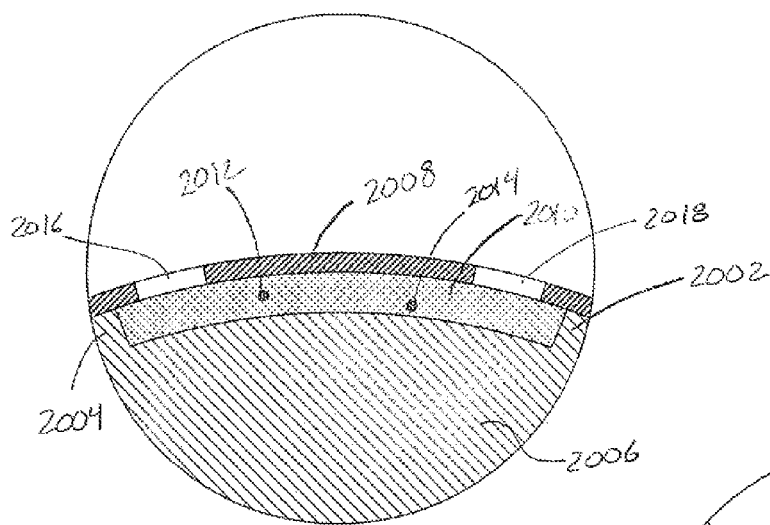
FIGS. 20A-20C show enlarged cross-sectional views of a chamber formed between a float and a tube wall with the contents of the chamber flushed to harvest a target material in accordance with one embodiment of the present invention.
Figure 20B:
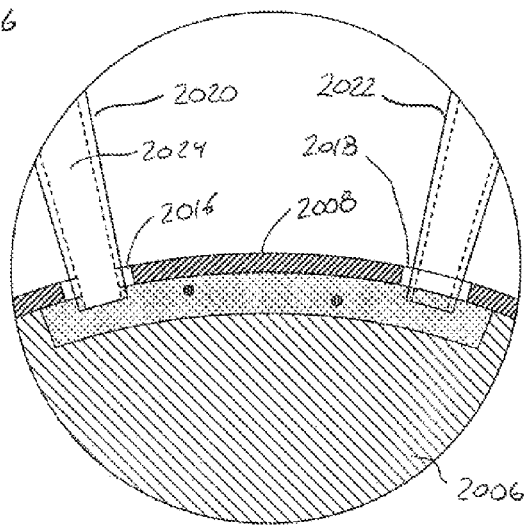
Figure 20C:
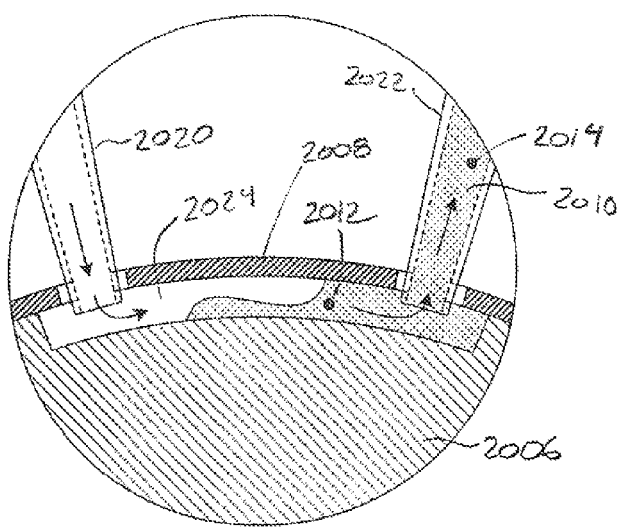

In order to facilitate harvesting of a target material, the openings may be formed to bracket the identified location of the target material and a suitable wash fluid, such as buffered saline solution, may be pumped into one of the openings while the wash containing the target material is flushed out through the other opening. FIGS. 20A-20C show enlarged cross-sectional views of a chamber formed between afloat and a tube wall with the contents of the chamber flushed to harvest a target material. In FIG. 20A, a chamber is formed between two splines 2002 and 2004, two ribs (not shown), the main body of a float 2006, and a tube 2008 wall. A fluid 2010 filling the chamber includes two target material particles 2012 and 2014. The target material particles 2012 and 2014 can be rare cancer cells, ova, inflammatory cells, viruses, parasites, or microorganisms. As shown in FIG. 2A, the tube 2008 wall includes a first opening 2016 and a second opening 2018 that can be formed by drilling or laser machining as described above, or by any other means that does not damage the target material. The diameter of the openings 2016 and 2018 can vary depending on the application. For example, the diameter of the openings 2016 and 2018 can vary from approximately 0.025 mm to approximately 2 mm or more. The openings 2016 and 2018 bracket or are located so that the target material particles 2012 and 2014 are located between the openings 2016 and 2018. In FIG. 20B, a first conduit 2020 is inserted into the first opening 2016 and a second conduit 2022 is inserted into the second opening 2018. The first conduit 2020 is filled with a suitable fluid wash 2024, such as a buffered saline solution, that is injected into the chamber while the second conduit 2022 is operated to create a vacuum that sucks or extracts the wash 2024, target material particles 2012 and 2014, and fluid 2010 filling the chamber. FIG. 20C shows a snapshot of the wash 2024 being injected into the chamber via the conduit 2020, while the wash 2024, target material particles 2012 and 2014, and fluid 2010 are being extracted via the conduit 2022. The conduits 2020 and 2022 can be tubes or two different pipettes with liquid delivery and extraction systems that can be operated to deliver a measured amount of wash to the chamber and measure the amount of wash and fluid extracted from the chamber.

Embodiments of the present invention are not limited to harvesting target materials from chambers of a float. The procedure described above with reference to FIG. 20 can also be used to harvest target materials from a helical channel formed by a helical ridge (see FIGS. 7, 8 and 9), a channel between two ribs (see FIGS. 6, 8, and 10), or a channel formed between two splines (see FIG. 12). The procedure can also be used to harvest target materials from a fluid filling an annular gap without ribs or splines, such as the floats shown in FIGS. 4, 5, and 14.

Figure 21:
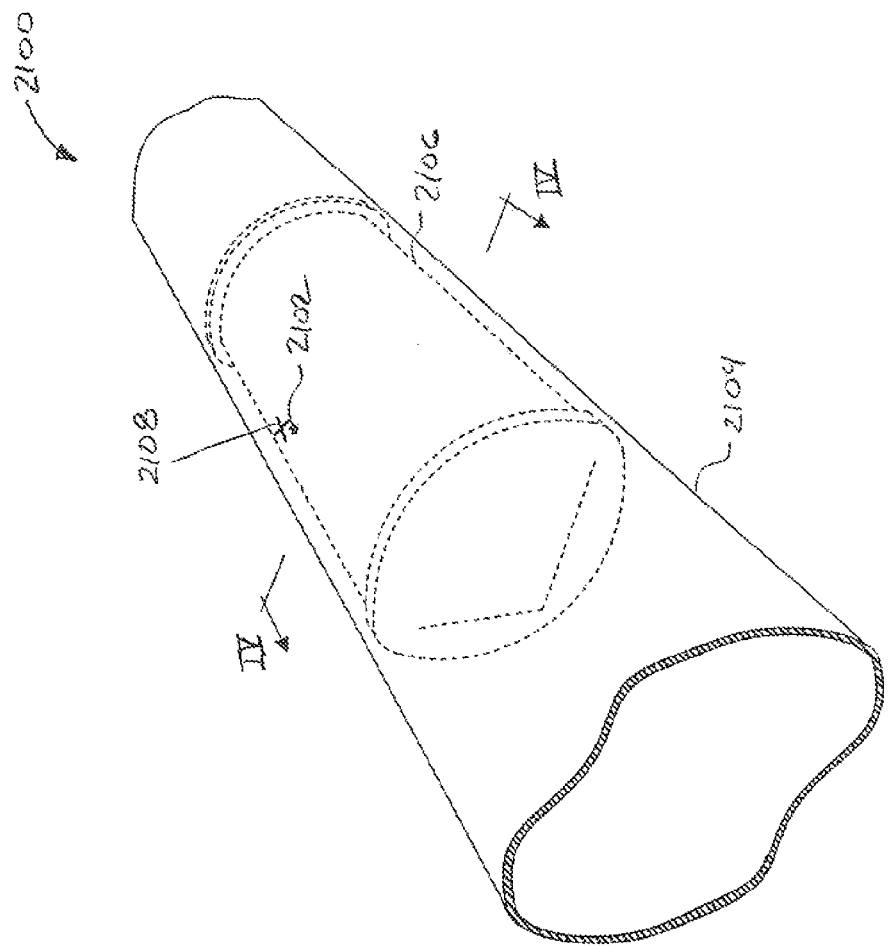
FIG. 21 shows an isometric view of a portion of a tube and float system in accordance with one embodiment of the present invention.

In alternative embodiments, a target material can be harvested by creating an opening over the identified location of the target material. FIG. 21 shows an isometric view of a portion of a tube and float system 2100. In FIG. 21, a target material particle 2102 is trapped in an annular gap formed by a tube 2104 inner wall and the main body of a float 2106. The particle 2102 can be a rare cancer cell, an ovum, fetal cell, an inflammatory cell, virus, parasite, or microorganism and includes a label. As shown in FIG. 21, the location of the particle 2102 is identified on the outer surface of the tube 2104 by a mark 2108 as described above in the preceding subsection. In alternative embodiments, the location of the particle 2102 can be identified by coordinates stored in memory or in another computer readable medium. The tube and float system 2100 can then be placed in a drill press, such as the drill press shown in FIG. 18A, but with the drill bit 1810 replaced by a coring drill bit.

Figure 22:
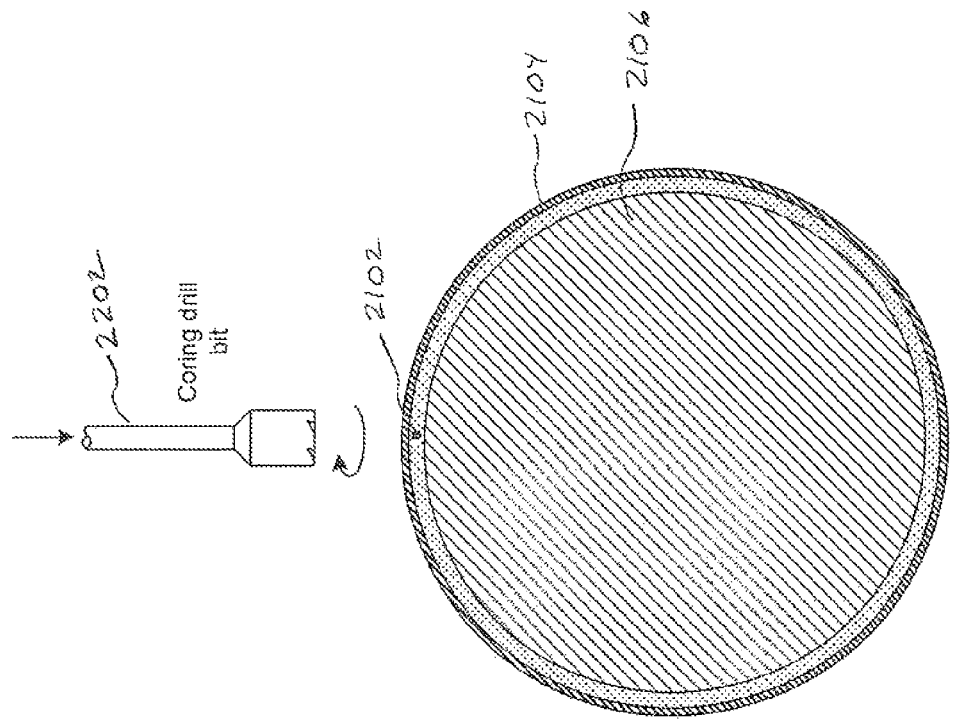
FIG. 22 shows an enlarged cross-sectional view of the tube and float system shown in FIG. 21, along a line IV-IV, in accordance with one embodiment of the present invention.

FIG. 22 shows an enlarged cross-sectional view of the tube and float system 2100 along a line IV-IV shown in FIG. 21. As shown in FIG. 22, the tube 2104 and float 2106 are oriented so that a coring drill bit 2202 is located above the location of the target material particle 2102. The coring drill bit 2202 is used to cut a ring-shaped opening in the tube 2104 wall leaving a portion of the tube wall called a "lid" above the particle 2102.

Figure 23:
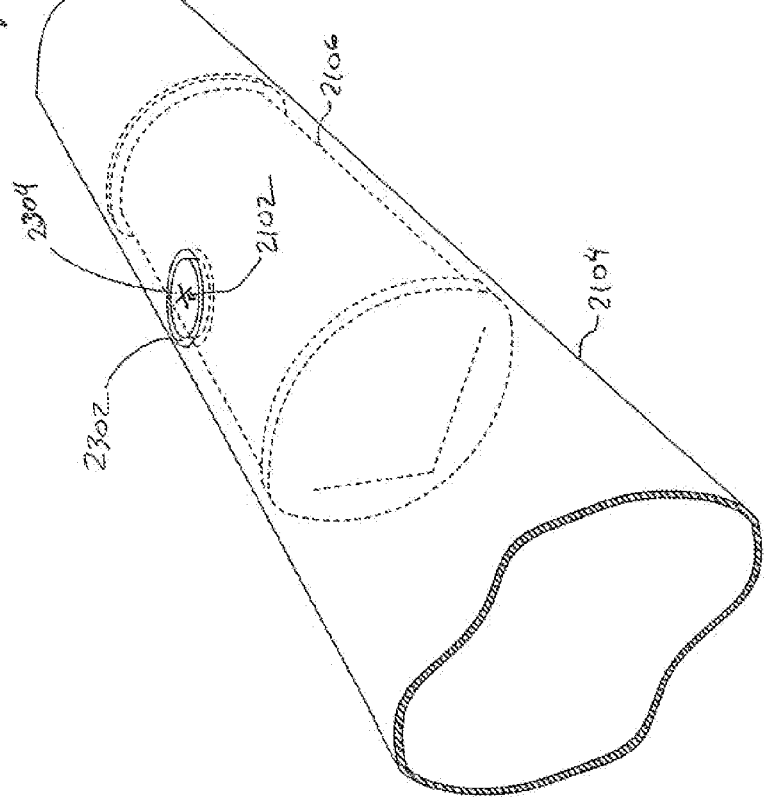
FIG. 23 shows an isometric view of the tube and float system shown in FIG. 22 after formation of a ring-shaped opening in a tube wall in accordance with one embodiment of the present invention.

FIG. 23 shows an isometric view of the tube and float system 2100 after the coring drill bit 2202 has been used to form a ring-shaped opening 2302 in the tube 2104 wall. The ring-shaped opening 2302 has a diameter large enough to extract the particle 2102. For example, the ring-shaped opening 2302 can have a diameter ranging from approximately 0.1 mm to approximately 2 mm. As shown in FIG. 23, a lid 2304 is formed by the coring drill bit 2202 and remains above the particle 2102. In other embodiments, the ring-shaped hole 2302 can also be formed using laser machining, as described above with reference to FIG. 19.

Figure 24:
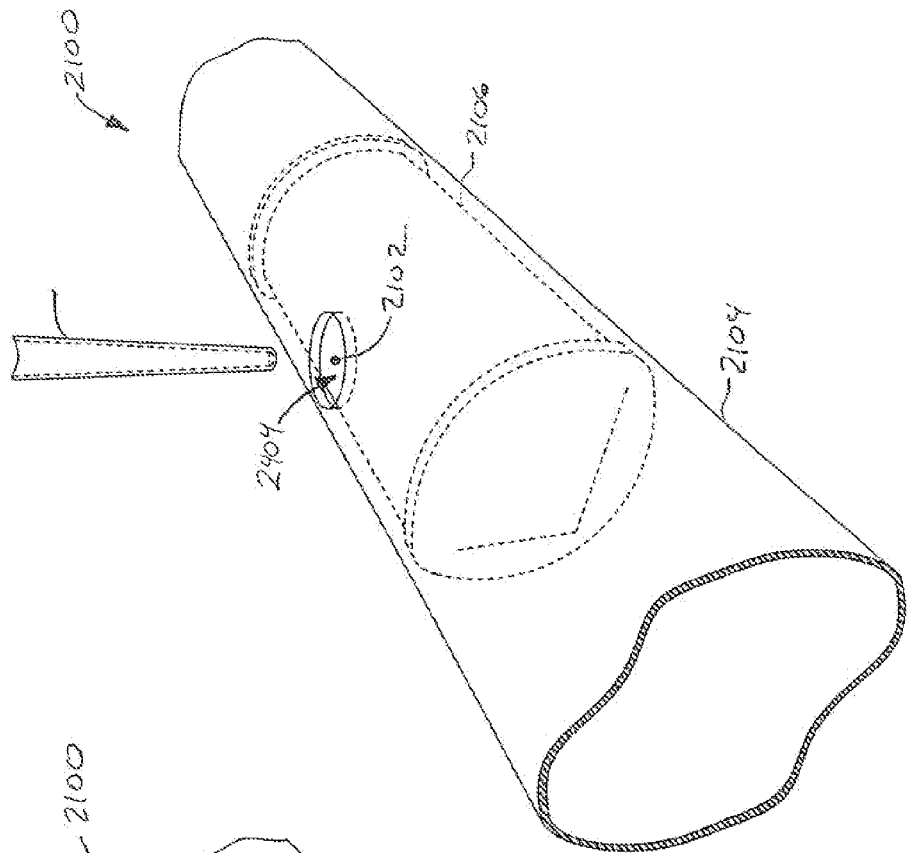
FIG. 24 shows an isometric view of the tube and float system shown in FIG. 22 with a lid removed exposing a target material particle in accordance with one embodiment of the present invention.

FIG. 24 shows an isometric view of the tube and float system 2100 with the lid 2304, shown in FIG. 23, removed exposing the target material particle 2102 within an opening or hole 2404. In certain embodiments, the target material particle 2102 can be harvested by extracting or sucking the contents of the fluid within the hole 2404 using a conduit, such as a pipette, through the opening 2404. In other embodiments, the particle 2102 can be extracted by applying pressure to the outside of tube 2104 around the hole 2404, causing the target material particle 2102 and other materials and fluid trapped in the annular gap around the hole 2404 to wash out. It may also be the case that the particle 2102 is attached to the lid 2304. The side of the lid 2304 facing the fluid trapped in the annular gap can be washed to remove any retained materials including any retained target material.

Figure 25:
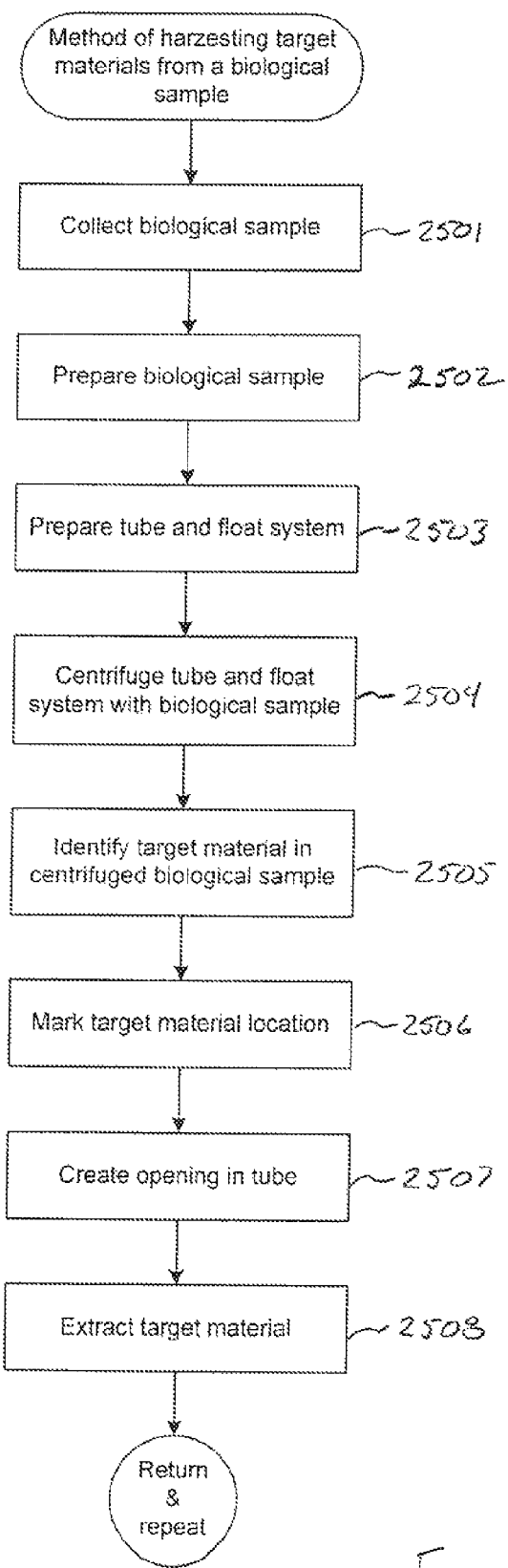
FIG. 25 shows a flow diagram summarizing a series of steps that can be used to harvest target materials from a suspension in accordance with one embodiment of the present invention.

FIG. 25 shows a flow diagram summarizing a series of steps that can be used to harvest target materials from a suspension. Note that methods of the present invention are not restricted to the following steps being performed in a particular order. The order in which a number of the following steps are performed can be interchanged. In step 2501, a suspension suspected of containing a target material is collected. The suspension can be a blood sample or any other kind of bodily fluid. In step 2502, the suspension is prepared by introducing a solution, mixture, or other suspension containing a label configured to attach to the target material. In step 2503, the suspension is combined in a tube with a float having a specific gravity that positions the float at approximately the same level as the layer containing the target material. In step 2504, the tube with the float and suspension are centrifuged in order to separate the various materials suspended in the biological along the axial length of the tube. If the target material is present, the float is positioned in, and expands the axial length of, the target material layer so that nearly the entire quantity of target material is trapped between the main body of the float and the inner surface of the tube. In step 2505, the material trapped between the main body of the float and the inner surface of tube is illuminated with light of a first frequency that causes the labels to emit light of a second frequency that can be detected, as described above with reference to FIG. 17. In step 2506, the location from which the light of the second frequency is emitted from the tube is identified and can be marked or coordinates corresponding to the location can be stored, as described above with reference to FIGS. 17 and 21. In step 2507, one or more holes are formed in the tube wall in close proximity to, or above, the place where the target material is believed to be located, as described above with reference to FIGS. 18, 19 and 22. In step 2508, the target material is extracted as described above with reference to FIGS. 20 and 24.

Note that method embodiments of the present invention provide the advantage of not using a force to separate target materials from other materials found in the same suspension. For example, for an immunomagnetic bead separation process, ligands and attached cells must be able to withstand the mechanical forces used during the removal or separation process of non-target cells. In immunomagnetic separation, both the magnetic forces used to extract the paramagnetic particles, and the forces connecting the paramagnetic particles to the labeled ligand all have to be sufficiently strong to allow capture and extraction of the rare cells. The total forces will be a function of the number of ligands and the affinity of the ligands on the rare cells surface as well as the strength of the magnetic field and the paramagnetic mass and properties of the attached particle. Antibodies coating paramagnetic beads bind to antigens that are present on the target cell surface, enabling the capture of target cells, which facilitates the concentration of the target cells. The concentration process is produced by a magnet placed on the side of the test tube. The magnet produces a magnetic field that draws the cells with paramagnetic beads attached to the magnet. On the other hand, methods of the present invention avoid the use of magnetic or electric fields to force the movement of a target material. Instead, for example, labeled cells are typically detectable relative to mature red blood cells, because rare cells typically have a density that is less than the density of mature red blood cells. In many instances, the difference in density is attributable to the rare cell containing a nucleus and a mature red blood cell does not have a nucleus. The presence of a sufficient number of epitopes for attachment of a detectable label or labels also facilitates detection. Embodiments of the present invention are not dependent upon the magnetic forces, the epitopes population density nor the affinity of the ligand to separate target cells from other cells or material in a blood sample. As a result, the number and affinity of the interactions of epitopes and ligands can be lower than that needed for immune/ligand/affinity capture techniques and such differences may permit the detection of malignant cells with lower amounts of epitomic density and therefore have greater clinical sensitivity Methods of the present invention have a number of additional advantages. The density gradient of the target material layer from which the target material particles are harvested is marked or noted and may have informational value. The detection and harvesting may be accomplished from a closed system that is free from contamination. The harvesting of a target material may be performed at the same time as, or within a short period of time after detection of the target material thereby facilitating the harvesting of live target material, such as live rare cells, whose biochemistry is intact. The harvesting of rare cells may be performed without the addition of any reagents or materials. For example, in the method described above with reference to FIG. 24, pressure is applied to the outside of the tube to force a target material of interest to an opening. The harvesting of target materials is independent of the number of and/or affinity of the surface epitope once detection is made, which is in contradistinction to affinity-based harvesting.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purposes of illustration and description. They are not intended to be exhaustive of or to limit the invention to the precise forms disclosed. Obviously, many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

The invention claimed is:

1. A method of harvesting a target material in a suspension, the method comprising:
    combining one or more labels with a suspension suspected of containing a target material in a tube, the one or more labels to differentiate the target material from other materials contained in the suspension;
    centrifuging the tube and suspension with a float having a specific gravity to position the float at approximately the same level as a layer containing the target material so as to cause individual target material particles present in the suspension to localize in a region between an outer surface of the float and inner wall of the tube;
    identifying approximate locations of the target material particles based on light emitted from the labels;
    marking the outer surface of the tube at points where the target material particles emit light; and
    extracting the target material particles through openings formed in the tube wall at marked locations of the tube.

2. The method of claim 1 farther comprising recording coordinates with respect to an indexing mark, each coordinate corresponding to a place on the surface of the tube where the target material particles emit light.

3. The method of claim 1 wherein identifying the approximate locations of target material particles farther comprises illuminating the region between the tube and float with one or more different wavelengths of light to cause labels attached to the target material particles to emit light that distinguishes the target material particles from other materials present in the suspension.

4. The method of claim 1, wherein identifying the location of the target material particles further comprises sorting the one or more wavelengths of light emitted from the labels in order to identify the one or more wavelengths emitted from the labels attached to the target material particles.

5. The method of claim 1, wherein extracting the target material through openings formed in the tube wall further comprises:
    forming a first opening and a second opening in the tube wall, the first opening and the second opening to bracket the approximate location of the target material particles;
    injecting a fluid wash into a region between the outer surface of the float and the inner wall of the tube through the first opening; and
    removing the fluid wash and target material particles located between the first opening and the second opening through the second opening.

6. The method of claim 5, wherein forming the first opening and the second opening in the tube wall further comprises drilling at least one hole in the tube wall using a drill.

7. The method of claim 5, wherein forming the first opening and the second opening in the tube wall further comprises laser machining at least one hole the tube wall using a laser.

8. The method of claim 5, wherein forming the first opening and the second opening in the tube wall further comprises melting at least one hole in the tube wall using a heating element.

9. The method of claim 5, wherein forming the first opening and the second opening in the tube wall further comprises puncturing at least one hole in the tube wall using a pointed object.

10. The method of claim 1, wherein extracting the target material through openings formed in the tube wall further comprises:
    forming a ring-shaped opening in the tube wall, the ring-shaped opening centered at the approximate location of one or more of the target material particles;
    removing a portion of the tube wall located within the ring-shaped opening leaving a hole to expose the one or more target material particles; and
    removing the one or more target material particles through the hole.

11. The method of claim 10, wherein forming the ring-shaped opening in the tube wall further comprises core drilling the ring-shaped opening in the tube wall using a coring drill bit.

12. The method of claim 10, wherein forming the ring-shaped opening in the tube wall further comprises laser machining the ring-shaped opening in the tube wall using a laser.

13. The method of claim 10, wherein removing the one or more target material particles through the hole further comprises sucking the at least one target material particle out through the hole using a pipette.

14. The method of claim 10, wherein removing the one or more target material particles through the hole further comprises applying pressure to the outside of the tube around the hole causing the at least one target material particle and any other fluid in and around the hole to wash out.

15. The method of claim 10 further comprises washing the portion of the tube wall to remove any retained materials including any retained target material particles.

16. A method of harvesting a target material in a suspension, the method comprising
    combining one or more labels with a suspension suspected of containing a target material in a tube, the one or more labels to differentiate the target material from other materials contained in the suspension;
    trapping the target material particles within a region formed between an outer surface of a float inserted into the tube and inner surface of the tube;
    illuminating the region with one or more different wavelengths of light that cause the labels attached to the target material particles to emit light that distinguishes the target material particles from other materials present in the suspension;
    forming a first opening and a second opening in the tube wall, the first opening and the second opening to bracket the approximate location of the target material particles;
    injecting a fluid wash into a region between the outer surface of the float and the inner wall of the tube through the first opening; and
    removing the fluid wash and target material particles located between the first opening and the second opening through the second opening, wherein the approximate locations of the target material particles correspond to where light is emitted from the labels attached to the target material particles.

17. The method of claim 16, wherein trapping the target material particles within a region formed between the outer surface of the float and the inner surface of the tube further comprises centrifuging the tube and suspension with the float having a specific gravity that positions the float at approximately the same level as a layer containing the target material so as to cause individual target material particles present in the suspension to localize in a region between the outer surface of the float and inner wall of the tube.

18. The method of claim 16, wherein identifying the approximate locations of target material particles further comprises illuminating the region between the tube and float with one or more different wavelengths of light to cause labels attached to the target material particles to emit light that distinguishes the target material particles from other materials present in the suspension.

19. The method of claim 16, wherein identifying the location of the target material particles further comprises sorting the one or more wavelengths of light emitted from the labels from the one or more wavelengths emitted from the labels attached to the target material particles.

20. The method of claim 16, wherein forming the first opening and the second opening in the tube wall further comprises drilling at least one hole in the tube wall using a drill.

21. The method of claim 16, wherein forming the first opening and the second opening in the tube wall further comprises laser machining at least one hole the tube wall using a laser.

22. The method of claim 16, wherein forming the first opening and the second opening in the tube wall further comprises melting at least one hole in the tube wall using a heating element.

23. The method of claim 16, wherein fowling the first opening and the second opening in the tube wall further comprises puncturing at least one hole in the tube wall using a pointed object.

24. The method of claim 16, wherein extracting the target material through openings formed in the tube wall further comprises:
   forming a ring-shaped opening in the tube wall, the ring-shaped opening centered at the approximate location of one or more of the target material particles;
   removing a portion of the tube wall located within the ring-shaped opening leaving a hole to expose the one or more target material particles; and
   removing the one or more target material particles through the hole.

25. The method of claim 24, wherein forming the ring-shaped opening in the tube wall further comprises core drilling the ring-shaped opening in the tube wall using a coring drill bit.

26. The method of claim 24, wherein forming the ring-shaped opening in the tube wall further comprises laser machining the ring-shaped opening in the tube wall using a laser.

27. The method of claim 24, wherein removing the one or more target material particles through the hole further comprises sucking the at least one target material particle out through the hole using a pipette.

28. The method of claim 24, wherein removing the one or more target material particles through the hole further comprises applying pressure to the outside of the tube around the hole causing the at least one target material particle and any other fluid in and around the hole to wash out.

29. The method of claim 24 further comprises washing the portion of the tube wall to remove any retained materials including any retained target material particles.

30. A method of harvesting a target material in a suspension, the method comprising:
   combining one or more labels with a suspension suspected of containing a target material in a tube, the one or more labels to differentiate the target material from other materials contained in the suspension;
   centrifuging the tube and suspension with a float having a specific gravity to position the float at approximately the same level as a layer containing the target material so as to cause individual target material particles present in the suspension to localize in a region between an outer surface of the float and inner wall of the tube;
   identifying approximate locations of the target material particles based on light emitted from the labels;
   recording coordinates with respect to an indexing mark, each coordinate corresponding to a location on the surface of the tube where the target material particles emit light; and
   extracting the target material particles through openings formed in the tube wall at recorded coordinates of the target material particles.

31. The method of claim 30 further comprising marking the outer surface of the tube at points where the target material particles emit light.

32. The method of claim 30, wherein identifying the approximate locations of target material particles further comprises illuminating the region between the tube and float with one or more different wavelengths of light to cause labels attached to the target material particles to emit light that distinguishes the target material particles from other materials present in the suspension.

33. The method of claim 30, wherein identifying the location of the target material particles further comprises sorting the one or more wavelengths of light emitted from the labels in order to identify the one or more wavelengths emitted from the labels attached to the target material particles.

34. The method of claim 30, wherein extracting the target material through openings formed in the tube wall further comprises:
   forming a first opening and a second opening in the tube wall, the first opening and the second opening to bracket the approximate location of the target material particles;
   injecting a fluid wash into a region between the outer surface of the float and the inner wall of the tube through the first opening; and
   removing the fluid wash and target material particles located between the first opening and the second opening through the second opening.

35. The method of claim 34, wherein forming the first opening and the second opening in the tube wall further comprises drilling at least one hole in the tube wall using a drill.

36. The method of claim 34, wherein forming the first opening and the second opening in the tube wall further comprises laser machining at least one hole the tube wall using a laser.

37. The method of claim 34, wherein forming the first opening and the second opening in the tube wall further comprises melting at least one hole in the tube wall using a heating element.

38. The method of claim 34, wherein forming the first opening and the second opening in the tube wall further comprises puncturing at least one hole in the tube wall using a pointed object.

39. The method of claim 1, wherein extracting the target material through openings fowled in the tube wall further comprises:
   forming a ring-shaped opening in the tube wall, the ring-shaped opening centered at the approximate location of one or more of the target material particles;

removing a portion of the tube wall located within the ring-shaped opening leaving a hole to expose the one or more target material particles; and removing the one or more target material particles through the hole.

40. The method of claim 39, wherein forming the ring-shaped opening in the tube wall further comprises core drilling the ring-shaped opening in the tube wall using a coring drill bit.

41. The method of claim 39, wherein forming the ring-shaped opening in the tube wall further comprises laser machining the ring-shaped opening in the tube wall using a laser.

42. The method of claim 39, wherein removing the one or more target material particles through the hole further comprises sucking the at least one target material particle out through the hole using a pipette.

43. The method of claim 39, wherein removing the one or more target material particles through the hole further comprises applying pressure to the outside of the tube around the hole causing the at least one target material particle and any other fluid in and around the hole to wash out.

44. The method of claim 39 further comprises washing the portion of the tube wall to remove any retained materials including any retained target material particles.

* * * * *